(12) United States Patent
Eitenmüller

(10) Patent No.: US 6,387,094 B1
(45) Date of Patent: May 14, 2002

(54) MEDICAL INSTRUMENT FOR DISSECTING TISSUE

(75) Inventor: Jürgen P. Eitenmüller, Castrop-Rauxel (DE)

(73) Assignee: Karl Storz GmbH & Co. KG (DE)

( * ) Notice: Subject to any disclaimer, the term of this patent is extended or adjusted under 35 U.S.C. 154(b) by 51 days.

(21) Appl. No.: 09/609,430

(22) Filed: Jun. 30, 2000

Related U.S. Application Data

(63) Continuation of application No. PCT/EP99/08008, filed on Oct. 21, 1999.

(30) Foreign Application Priority Data

Oct. 30, 1998 (DE) .......................... 198 50 068

(51) Int. Cl.$^7$ .............................................. A61B 18/18
(52) U.S. Cl. .............................. 606/48; 606/50; 606/45
(58) Field of Search ................... 606/41, 45–52

(56) References Cited

U.S. PATENT DOCUMENTS

| | | | |
|---|---|---|---|
| 4,985,030 A | 1/1991 | Melzer et al. ................. | 606/51 |
| 5,330,471 A * | 7/1994 | Eggers ......................... | 606/32 |
| 5,360,428 A * | 11/1994 | Hutchinson, Jr. ............. | 606/41 |
| 5,779,701 A * | 7/1998 | McBrayer et al. ............. | 606/46 |
| RE36,795 E * | 7/2000 | Rydell ......................... | 606/45 |

FOREIGN PATENT DOCUMENTS

| | | |
|---|---|---|
| DE | 2415263 | 10/1975 |
| DE | 0 400 288 | 3/1990 |
| DE | 198 50 068 | 6/2000 |
| WO | WO 93/04635 | 3/1993 |
| WO | WO 96/22056 | 7/1996 |

* cited by examiner

Primary Examiner—Roy Gibson
(74) Attorney, Agent, or Firm—St. Onge Steward Johnston & Reens LLC

(57) ABSTRACT

A medical instrument for dissecting tissue in the human or animal body has an elongated shaft and, at a distal end of said shaft, two jaw parts that are movable relative to one another and that coact for dissecting tissue, at least one of said jaw parts being configured as an electrode which can be impinged upon by high-frequency current. A further electrode that can be impinged upon by high-frequency current is provided, and can be displaced optionally from a retracted proximal position into a distal position adjacent to said jaw parts in which position it forms, in coaction with said at least one jaw part configured as an electrode, one pole of an electrode arrangement for bipollar coagulation of tissue

18 Claims, 4 Drawing Sheets

MEDICAL INSTRUMENT FOR DISSECTING TISSUE

CROSS-REFERENCE TO PENDING APPLICATION

This is a continuation of pending International Application PCT/EP99/08008. Oct. 21, 1999.

BACKGROUND OF THE INVENTION

The present invention relates to a medical instrument for dissecting tissue in the human or animal body, having an elongated shaft and having at the distal end of the shaft two jaw parts that are movable relative to one another and that coact cuttingly and/or graspingly, at least one of the jaw parts being configured as an electrode which can be impinged upon by high-frequency current.

"Dissecting" for the purposes of the present invention is understood to mean the cutting of tissue and/or grasping or gripping of tissue in order to cut of f tissue in the body and remove it or set it aside.

An instrument of this kind is preferably used in minimally invasive surgery in which, in contrast to conventional open surgery, the instrument is guided from outside through a small incision into the surgical area, the surgical procedure being performed under endoscopic monitoring.

In such an instrument, often not only is the purely mechanical effect of the jaw parts used to cut off or cut through tissue, but the jaw parts or at least one of the jaw parts can additionally be impinged upon by monopolar high-frequency current so as on the one hand to enhance the cutting effect by way of the thermal effect of the high-frequency current in the tissue, and on the other hand to bring about coagulation of the tissue at the cutting point generating heat , so as to reduce or even eliminate the bleeding that occurs when the tissue is cut through.

While at first only the dissection of smaller portions of tissue could be performed successfully in minimally invasive surgery, the development of minimally invasive surgery is now moving toward removing even larger portions of tissue, for example the large intestine or organs. When removing larger portions of tissue, it is also necessary to cut through larger tissue bridges, which moreover may contain larger vessels. The more severe bleeding that possibly occurs in this context cannot be managed, however, with the monopolar-mode instrument, so that it is additionally necessary, when cutting through larger tissue bridges, to use bipolar-mode coagulation instruments.

This means, however, that while dissecting (i.e. in order to cut through such larger tissue bridges), the surgeon must make an instrument change several times if he or she does not was to rely only on the lesser coagulating effect of the monopolar-mode instrument. The operation thus proceeds in such a way that the surgeon removes tissue principally with the monopolar-mode instrument and, when he or she arrives at a tissue bridge containing a larger vessel, must remove the monopolar-mode cutting instrument from the patient's body and bring to the operating location a bipolar-mode coagulation instrument. This instrument change is, however, cumbersome, extends the length of the procedure quite considerably in some cases, and increases the risk of complications.

There is known, from the catalog of the German company styled Karl Storz GmbH & Co., Tuttlingen entitled "Karl Storz-Endoskope," Gynecology volume 2/96, page BI/COA 5/7, a bipolar coagulation instrument that has at the distal end two pairs of jaw parts spaced apart from one another, each pair of which is configured as an electrode that can be impinged upon by high-frequency current. The two jaw part pairs are spaced apart from one another and can therefore be operated as a bipolar electrode arrangement. Arranged between the jaw part pairs is a cutting tool in the form of a scalpel that is selectably movable back and forth. With this instrument, a vessel can be clamped between the two jaw part pairs and coagulated, and then cut through by advancing the cutting tool. This instrument is, however, less suitable for being used principally as a dissecting instrument for cutting through tissue. Instead, the principal function of this instrument is bipolar coagulation.

Instruments similar to this are described in WO 95/15124 and U.S. Pat. No. 5,445,638.

In the case of the known instruments cited above, the cutting effect by way of the displaceable scalpel arranged between the coagulation electrodes is purely mechanical, i.e. with no assistance from high-frequency current. In addition, these cutting devices are predominantly suitable only for cutting through vessels, but not for making longer cuts and also not for grasping.

For the purpose cited initially of dissecting tissue in the human or animal body, in which larger portions of tissue are removed and large tissue bridges need to be cut through for the purpose, an instrument of the kind cited initially is therefore functionally correct, since with such an instrument the cutting through of tissue is to the fore.

It is therefore the object of the invention to develop an instrument of the kind cited initially in such a way that with this instrument even larger portions of tissue, and thus larger tissue bridges containing larger vessels, can be cut through with no risk of excessive bleeding.

SUMMARY OF THE INVENTION

According to the present invention this object is achieved by a medical instrument comprising:
  an elongated shaft having a distal end;
  two jaw parts at said distal end of said shaft, said two jaw parts being movable relative to one another and configured to coact for dissecting said tissue, at least one of said two jaw parts being configured as an electrode which can be impinged upon by high-frequency current,
wherein a further electrode which can be impinged upon by a high-frequency current is provided which can be optionally displaced from a retracted proximal position into a distal position adjacent to said two jaw parts in which position said further electrode forms in coaction with said at least one jaw part configured as an electrode one pole of an electrode arrangement for bipolar coagulation of said tissue.

What is therefore made available according to the present invention is an instrument with which it is possible, while using a monopolar-mode instrument in standard fashion, to dissect tissue by cutting and/or grasping, and if necessary to coagulate very small vessels in conventionally monopolar fashion.

If, however, the surgeon encounters a tissue bridge which appears to contain larger vessels, this tissue bridge can be gripped between the jaw parts and the further electrode by advancing the further electrode into the distal position adjacent to the jaw parts. The at least one jaw part configured as an electrode and the further electrode can then be impinged upon by high-frequency current so that the tissue lying therebetween can be coagulated in bipolar fashion. In other words, the jaw parts form the one electrode pole and the further electrode the second electrode pole. Then, preferably after the further electrode has been slid back into its proximal position, dissection can continue with the jaw parts, either purely mechanically or under the action of monopolar current. The invention thus makes available an instrument operable in monopolar fashion for dissecting tissue, in combination with a selectably or optionally connectable bipolar coagulation device, thus achieving the considerable advantage that an instrument change is not necessary for dissection and for bipolar coagulation, and larger portions of tissue can also be dissected quickly and safely while preventing bleeding.

The underlying object of the invention is thus completely achieved.

In a preferred embodiment, the jaw parts are curved out of a longitudinal axis of the shaft, and the further electrode is arranged on a concave side of the jaw parts.

The advantage of this feature is that when the further electrode is advanced to its distal position, the tissue to be coagulated in bipolar fashion can be securely grasped and held between the jaw parts and the further electrode. The curved configuration of the jaw parts acts in this context as a catch hook and backstop preventing the tissue from escaping laterally as the further electrode is advanced.

In a further preferred embodiment, the further electrode is of planar configuration and has approximately the same width dimension as the two jaw parts.

The advantage here is that larger portions of tissue can be coagulated with only one coagulating operation. Of course it is also possible to coagulate several times, shifting the instrument laterally, if a particularly large tissue bridge containing particularly large vessels needs to be cut through. The jaw parts can be open or closed during bipolar coagulation of the tissue, the effective electrode surface of the jaw parts being increased even further when the jaw parts are in the open position.

In a further preferred embodiment the further electrode forms, with at least one of the jaw parts, a catching space for gripping tissue.

The advantage of this configuration is that even thicker tissue and even thicker vessels can be grasped between the further electrode and the jaw parts.

In a further preferred embodiment, the further electrode, in its retracted position, is received in recessed fashion in the shaft.

The advantage here is that in its retracted position, the further electrode does not impede the dissection of tissue using the two jaw parts (which is what is predominantly to be performed with the instrument), and is slid out of the shaft only as necessary.

In a further preferred embodiment, the further electrode is beveled at its distal end on a side facing toward the jaw parts.

The advantage here is that as the further electrode is advanced, the tissue to be grasped between the jaw parts and the further electrode is prevented from being displaced by the further electrode so that it then cannot be coagulated between the further electrode and the jaw parts. The aforementioned curved configuration of the jaw parts is also particularly advantageous in this context, since the concave side of the jaw parts acts in the manner of a catch hook and backstop as the further electrode is advanced, so that the tissue cannot escape laterally as the further electrode is advanced.

In a further preferred embodiment, the further electrode is of at least partially flexible configuration and describes, when advanced, a trajectory that initially runs approximately in longitudinal direction of the shaft with or without a component turned slightly away from the jaw parts, and before reaching the distal position runs with a component directed toward the jaw parts.

The advantage of the flexible configuration of the electrode is that the electrode, when advanced, describes a curved trajectory as a result of suitable guidance or because of a preload imparted to the electrode, so that the tissue to be coagulated can be more easily gripped during advancement and, in the maximally advanced distal position, can be securely held or clamped between the jaw parts and the further electrode.

In this context, it is preferred in one exemplary embodiment if there is arranged on the shaft a cam bevel onto which a cam bevel configured on the further electrode runs as the further electrode is advanced, thus pressing the further electrode toward the jaw parts in the distal position.

What is advantageously achieved thereby is that the tissue can be held with a greater clamping force between the maximally advanced further electrode and the jaw parts.

In a further preferred exemplary embodiment, a cam bevel is arranged on the shaft so that as the further electrode is advanced, it is first spread away from the jaw parts and, in the distal position, deflects elastically toward the jaw parts.

The advantage of this embodiment is that as it advances, the further electrode can first be advanced in a direction away from the jaw parts, so that in turn even larger portions of tissue can be securely grasped. Because the further electrode elastically deflects, in its distal position, toward the two jaw parts, the grasped tissue is then automatically held securely between the jaw parts and the further electrode for bipolar coagulation.

In a further preferred embodiment, there is arranged at the proximal end of the instrument a handle that has two grip elements for actuation of the jaw parts and a further grip element for actuation of the further electrode, the grip elements forming a grip arrangement operable with one hand.

The advantage of this feature is that actuation of the jaw parts on the one hand, and selectable actuation of the further electrode (i.e. advancing and retracting the further electrode), can be performed particularly conveniently and, above all, by one-handed operation. This improves the handling of the instrument according to the present invention, and makes it possible to work in fatigue-free fashion with the instrument.

It is preferred in this context if the further grip element is joined via a lever arrangement to the further electrode in such a way that by pulling the further grip element, the further electrode is slid from its proximal into its distal position.

This configuration of the further grip element further improves the handling of the instrument, since an actuation of the further grip element by tension in order to advance the further electrode makes possible better apportioning of force and thus more reliable operation with the instrument.

In a further preferred embodiment, the further electrode is preloaded into its proximal position, into which it automatically returns after the further grip element is released.

This feature further improves the handling of the instrument according to the present invention.

In a further preferred embodiment, the further electrode is joined to the further grip element via an actuation element received in axially movable fashion in the shaft, the actuation element furthermore being joined via a wiper contact to a high-frequency current lead-in.

What results therefrom, because of the axially movable actuation element, is on the one hand a particularly advantageous energy transfer between the further grip element and the further electrode, and on the other hand, as a result of the wiper contact, an advantageously physically simple and reliable application of current to the further electrode as a result of the delivery of current through the movable actuation element.

In a preferred embodiment, the wiper contact allows the passage of current to the further electrode only when the electrode has been advanced into or almost into the distal position.

This embodiment advantageously improves the operating reliability of the instrument according to the present invention.

In a further preferred embodiment, the actuation element is joined to the further grip element removably, preferably by snap-locking.

The advantage here is to make possible easy disassembly of the instrument in terms of the coagulation device provided according to the present invention.

In a further preferred embodiment, the jaw parts are removably joined to the grip elements by way of an actuation element received in axially movable fashion in the shaft.

This feature further improves the disassembly capability of the instrument according to the present invention, so that the instrument according to the present invention can easily be cleaned and thus fully satisfies the stringent hygiene requirements in terms of sterility.

It is preferred in this context if the jaw parts are joined to the distal end of the shaft via a bayonet closure.

This configuration of the join between the jaw parts and the shaft creates a configuration that is advantageously easy to operate in order to join the jaw parts to and detach them from the shaft.

It is particularly preferred if the instrument can be disassembled into the subassemblies made up of the jaw parts with the actuation element joined thereto, the further electrode with the further actuation element, the handle, and the shaft.

As a result of this ability of the instrument to be disassembled into the aforesaid four subassemblies, the instrument according to the present invention can be cleaned particularly thoroughly and thus meets the most stringent hygiene requirements.

Further advantages are evident from the description below and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description which follows. In the drawings.

DETAILED DESCRIPTION OF PREFERRED EMBODIMENTS

Figure 1:
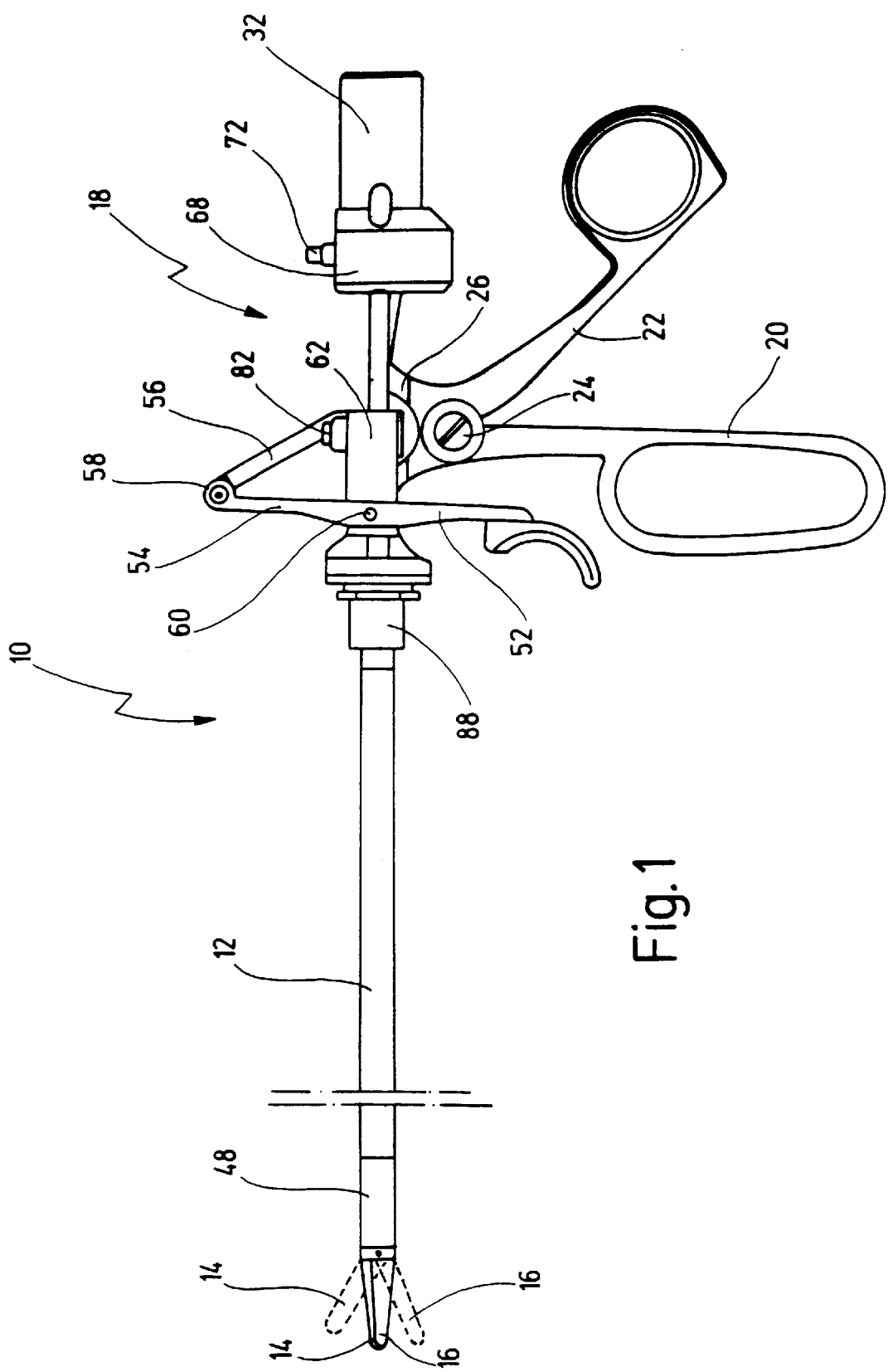
FIG. 1 shows an overall side view of a medical instrument for dissecting tissue.

FIG. 1 shows a medical instrument, labeled with the general reference character 10, for dissecting tissue in the human or animal body. Portions of instrument 10 are shown in detail in the further FIGS. 2 through 7.

Instrument 10 is used in minimally invasive surgery to cut and detach tissue, and is suitable in particular for dissecting large portions of tissue in the dissection of which larger tissue bridges, which may also contain larger vessels, must be cut through.

Instrument 10 has an elongated shaft 12. Shaft 12 is configured substantially as a cylindrical tube.

Two jaw parts 14 and 16 that are movable relative to one another are arranged at the distal end of shaft 12; in the exemplary embodiment shown, both jaw parts 14 and 16 are movable. Also possible, however, is an embodiment in which only one of the jaw parts—either jaw part 14 or jaw part 16—is movable.

Jaw parts 14 and 16 coact as a cutting tool in order to cut through tissue. Jaw parts 14 and 16 are shown in FIG. 1 with solid lines in their closed position and with dashed lines in their open position. Jaw parts 14 and 16 can also be configured as grasping or gripping tools rather than as cutting tools, or as a combination of cutting and grasping tools.

Figure 4:
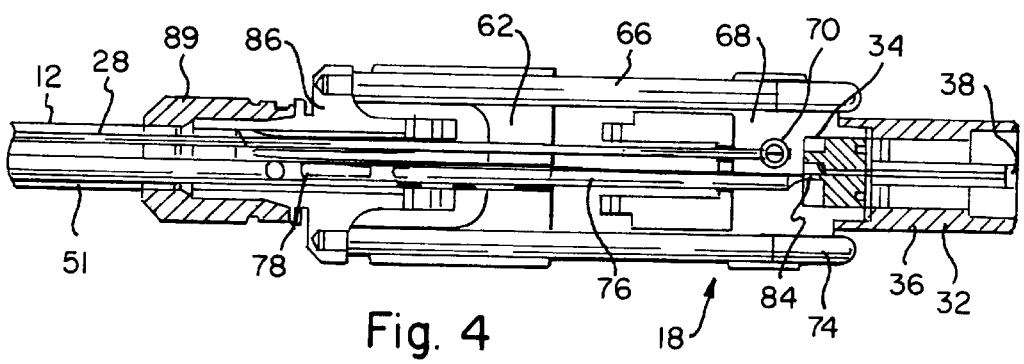
FIG. 4 shows a plan view of a handling region of the instrument in FIG. 1, partially in section.
Figure 5:
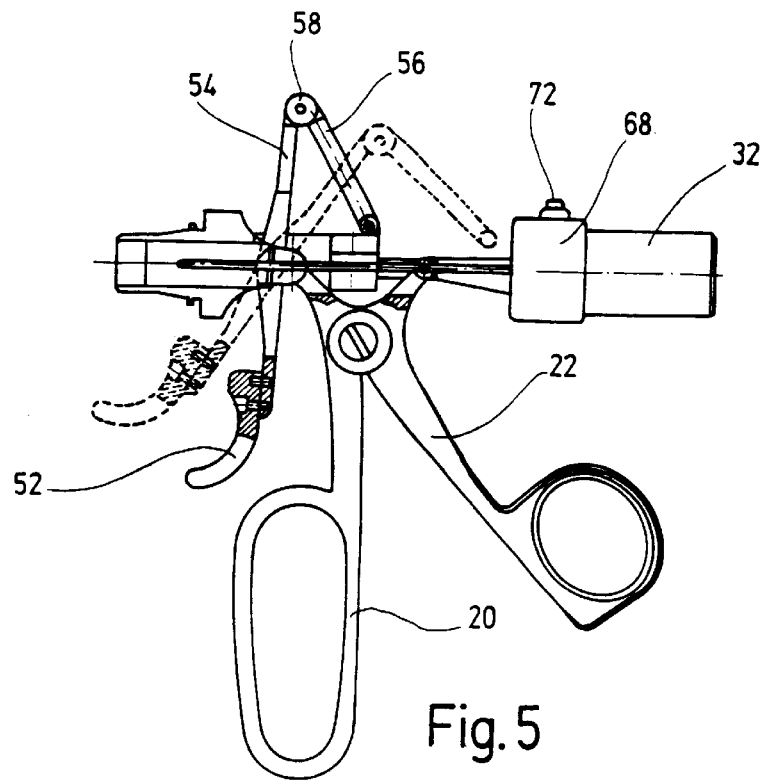
FIG. 5 shows the handle of the instrument, in isolation, in a side view.

At the proximal end of shaft 12, instrument 10 has a handle labeled with the general reference character 18. Handle 18 is shown in FIG. 5 in isolation in a side view, and in FIG. 4 in a partially sectioned plan view with shaft 12 attached thereto, only the proximal end of shaft 12 being shown in FIG. 4.

Figure 2:
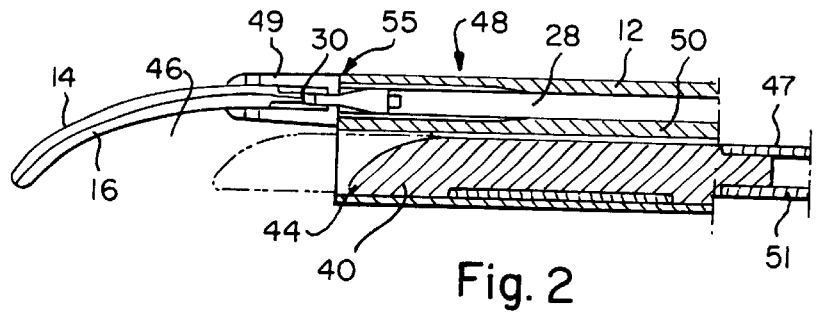
FIG. 2 shows a longitudinal section through the distal end of the instrument in FIG. 1 in a view rotated 90° (plan view), the further electrode being shown in its retracted proximal position.

Handle 18 has a first grip element 20 and a second grip element 22, grip elements 20 and 22 serving to actuate jaw parts 14 and 16 in order to open and close them. Grip element 20 is immovable, i.e. secured to the shaft, whereas grip element 22 is movable. Grip elements 20 and 22 are joined to one another via a joint 24. One limb 26 of movable grip element 22 is nonpositively joined, as shown in FIG. 4 and FIG. 2, to jaw parts 14 and 16 via an actuation element 28 received in axially displaceable fashion in shaft 12. Actuation element 28 works to open jaw parts 14 and 16 when pressed, and by closing movable grip element 22 toward immovable grip element 20, actuation element 28 is displaced in the proximal direction by limb 26, thus closing jaw parts 24 and 26. Actuation element 28 engages on a toggle lever arrangement 30 at the proximal end of jaw parts 14 and 16 which opens and closes jaw parts 14 and 16.

In addition, at least one of jaw parts 14 and 16, but preferably both jaw parts 14 and 16, are configured as electrodes which can be impinged upon by high-frequency current, i.e. to which high-frequency current can be applied, a high-frequency current connector 32 for connecting a high-frequency current cable (not shown) being provided at the proximal end of instrument 10. Current is fed in through a current lead 34 through actuation element 28 to one of jaw parts 14 or 16 or to both jaw parts 14 and 16. For that purpose, actuation element 28 is correspondingly insulated from shaft 12. Either jaw parts 14 and 16 can be impinged upon by monopolar high-frequency current in order to cut tissue in monopolar fashion, or jaw parts 14 and 16 serve as the counterelectrode or counterpole for a bipolar coagulation of tissue, as will be described below.

High-frequency current connector 32 comprises a housing 36 made of plastic in which the actual contact finger 38 is received in recessed fashion.

As already mentioned earlier, not only does instrument 10 have the function of cutting through tissue using jaw parts 14 and 16, but it is also possible to coagulate in bipolar fashion with instrument 10.

Figure 3:
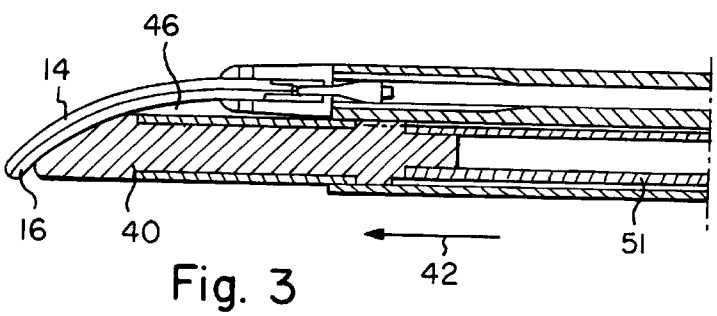
FIG. 3 shows a representation corresponding to that of FIG. 2, with the further electrode advanced distally.

For that purpose, instrument 10 has a further electrode 40, to which high-frequency current can be applied, that is visible in FIGS. 2 and 3. Electrode 40 is not visible in the representation of FIG. 1, since further electrode 40 is arranged alongside jaw parts 14 and 16 and is concealed by them in FIG. 1.

Further electrode 40 is shown in FIG. 2 in its maximally proximally retracted position in which further electrode 40 is received in recessed fashion in shaft 12. In FIG. 3, further electrode 40 is advanced (as shown by an arrow 42) into its distal position in which it forms, in coaction with the at least one jaw part 14 or 16 configured as an electrode, or with both jaw parts 14 and 16, the second pole of an electrode arrangement of a bipolar coagulation tool, the at least one jaw part 14 or 16 or both jaw parts 14 and 16 forming the first pole.

Further electrode 40 is configured with a bevel at its distal end 44.

Jaw parts 14 and 16 are furthermore configured so as to curve out of the longitudinal axis of shaft 12, further electrode 40 being arranged on the concave side of jaw parts 14 and 16. When further electrode 40 is advanced, curved jaw parts 14 and 16 serve to retain, in the manner of a catch hook, the tissue that is to be brought between further electrode 40 and jaw parts 14 and 16; the oblique configuration of distal end 44 of further electrode 40 also contributes to the formation between further electrode 40 and jaw parts 14 and 16 of a catching space 46 in which the tissue that is then to be coagulated in bipolar fashion is caught. This is also evident from FIG. 3, in which catching space 46 remains as an open space between further electrode 40 and jaw parts 14 and 16 even when further electrode 40 is in the maximally distally displaced position. At the proximal end, electrode 40 has a low-friction layer 47 and insulating layer made of plastic.

Further electrode 40 is of planar configuration in the direction transverse to the drawing plane of FIGS. 2 and 3, and in that dimension has approximately the same width dimension as the two jaw parts 14 and 16.

The embodiment of further electrode 40 shown in FIGS. 2 and 3 is rigid and solid.

In the region of its distal end, shaft 12 has a bushing 48 that, as shown in FIG. 2, has a partition wall 50 with which actuation element 28 and further electrode 40 are separated from one another. In the segment of shaft 12 proximally adjoining bushing 48, shaft 12 is configured without such a partition wall. Bushing 48 is immovably joined to the remaining portion of shaft 12. Jaw parts 14, 16 and actuation element 28 joined to them are joined detachably (by way of a 90° rotation) to bushing 48 via a bayonet closure 55 (not shown in further detail) that is configured on a fork 49.

For actuation of further electrode 40, the latter is joined via an actuation element 51 in the form of a thin tube to a further grip element 52 on handle 18. Further grip element 52 forms, with grip elements 20 and 22, a grip arrangement that is operable with one hand. Grip element 52 is arranged on the distal side of grip elements 20 and 22, and is configured in the manner of a pistol trigger that can be conveniently operated, for example, with the index finger. Grip element 22 can be operated with the thumb, and grip element 20 can be operated, for example, with the middle finger or with the middle finger and additionally the ring finger. It is thus not necessary to shift one's grip or change the hand position in order to actuate jaw parts 14 and 16 or to advance or retract electrode 40.

The further grip element is joined to actuation element 51 via a lever arrangement made up of a first lever 54 and a second lever 56. First lever 54 and second lever 56 are joined to one another via a joint 58. First lever 54 is pivotable about a rotation point 60 with respect to shaft 12. Second lever 56 is attached at its end opposite joint 58 to a carriage 62 that in turn is detachably joined to actuation element 51.

In FIG. 5, grip element 52 for actuation of further electrode is shown with dashed lines in a position in which further electrode 40 as shown in FIG. 2 is received in shaft 12 in its proximal position. When grip element 52 is pulled in the proximal direction into the position shown in FIG. 5 with solid lines, the lever arrangement made up of levers 54 and 56 brings about a reversal of movement, so that carriage 62 and (via actuation element 51) further electrode 40 are displaced in the distal direction. Carriage 62 slides on guide rods 66, arranged laterally on handle 18, that pass through orifices 64 in carriage 62.

The actuation travel of carriage 62 and thus of further electrode 40 is approximately 2.5 cm. During the movement of carriage 62, high-frequency current connector 32 remains stationary if jaw parts 14 and 16 are not actuated by way of grip elements 20 and 22.

As has already been described earlier, jaw parts 14 and 16 are joined to movable grip element 22 via an actuation element 28. Limb 26 of movable grip element 22 is joined to a further carriage 68 to which actuation element 28 is fastened by way of a snap catch 70. At the proximal end of carriage 68, high-frequency current connector 32 is immovably joined thereto. A snap-lock button 72 (cf. FIG. 1) is used to release the snap-lock connection between actuation element 28 and carriage 68 so that jaw parts 14, 16, with actuation element 28, can be pulled in the distal direction out of shaft 12 once the bayonet closure has been undone by rotating jaw parts 14, 16 through 90°.

Carriage 68, like carriage 62, is axially displaceable on guide rods 66, for which purpose sleeves 74, into which guide rods 66 engage, are mounted on carriage 68. Actuation element 28 is thus axially displaced upon actuation of grip element 22; unlike the actuation travel of actuation element 52, the actuation travel of actuation element 28 is substantially smaller, being only a few millimeters.

Actuation element 51 for axial displacement of further electrode 40 is furthermore joined to a high-frequency current lead-in 76. High-frequency current lead-in 76 has a rod that has a wiper contact 78 at its distal end. Actuation element 51 is slid over wiper contact 78 onto high-frequency current leadin 76 as far as carriage 62, where actuation element 51 is snap-locked to carriage 62 by way of a snap catch 80 (cf. FIG. 7). A snap-lock button 82 is once again provided in order to undo the snap-lock connection between actuation element 51 and carriage 62, so that once snap catch 80 has been released, pressing down snap-lock button 82 allows actuation element 51 to be pulled in the distal direction out of shaft 12.

High-frequency current lead-in 76 is connected via a further current lead 84 to contact finger 38 of the high-frequency current connector.

Wiper contact 78 coacts with actuation element 51 in such a way that current transfer from high-frequency current lead-in 76 to actuation element 51 and thus to the further electrode becomes possible only when actuation element 51 and thus further electrode 40 have almost reached their maximally distal position. This is achieved by the fact that wiper contact 78 engages onto an insulating layer on actuation element 51 when the actuation element is in the proximal position, and engages onto metal only when electrode 40 is almost in its distal position.

Figure 6:
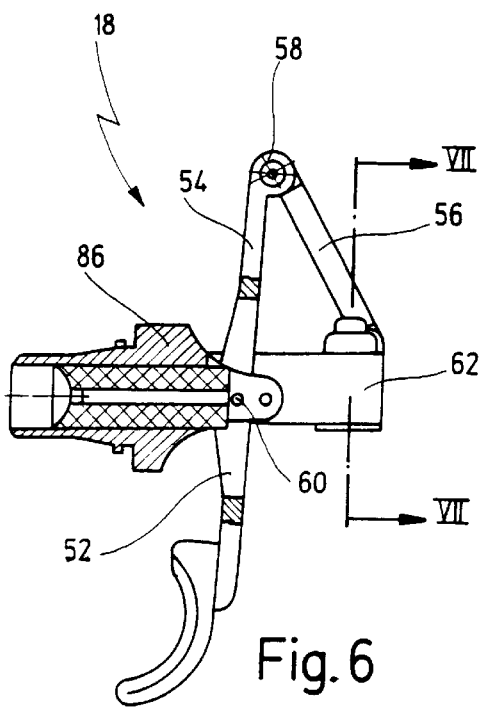
FIG. 6 shows, in isolation, a portion of the handle in FIG. 5, showing the further grip element for actuation of the further electrode.
Figure 7:
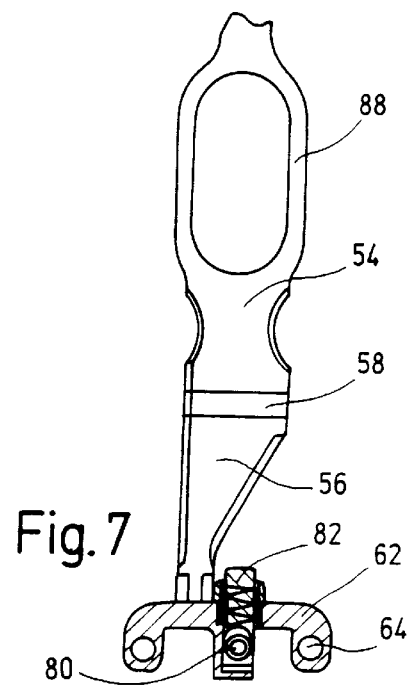
FIG. 7 shows a section along line VII—VII in FIG. 6, the further grip element being shown in the folded-out position.

As shown in FIGS. 4 and 6, handle 18 has at its distal end a housing segment 86 to which on the one hand guide rods 66 (cf. FIG. 4) and on the other hand first lever 54 of further handle element 52 are attached. It is further evident from FIG. 7, in which further grip element 52 is shown in the position swung up around joint 58, that first lever 54 of grip element 52 has an annular bifurcation 88 so that first lever 54 fits around the arrangement made up of actuation element 28 and actuation element 51.

Further electrode 40 is preloaded into its proximal position shown in FIG. 2. This is achieved, in this exemplary embodiment, by the fact that joint 58 of the lever arrangement made up of levers 54 and 56 is under spring pressure, which acts in such a way that levers 54 and 56 are always pushed apart from one another (representation with dashed lines in FIG. 5).

While it has already been mentioned that actuation element 28 and actuation element 51 are removable from handle 18, shaft 12 is also joined removably to handle 18, this being done by a coupling 89 (cf. FIGS. 1 and 4) with which shaft 12 is thread-joined onto housing 86 of handle 18 or is joined thereto in the manner of a bayonet closure.

Instrument 10 can be used on the one hand for dissecting tissue using jaw parts 14 and 16, for example in order to cut through or cut off portions of tissue. In this context, only grip elements 20 and 22 are actuated in order to open or close jaw parts 14 and 16. If a larger tissue bridge that possibly contains larger vessels is then encountered, bipolar coagulation can first be performed with instrument 10 before cutting through a larger tissue bridge of this kind. This is done by actuating grip element 52, as a result of which further electrode 40 is displaced in the distal direction out of shaft 12 and forms, with jaw parts 14 and 16, an electrode arrangement for bipolar coagulation. By applying current to further electrode 40 and to jaw parts 14 and 16—or, as described earlier, to only one of jaw parts 14 and 16—the tissue gripped between jaw parts 14 and 16 and further electrode 40 can be coagulated in bipolar fashion. Then, after grip element 52 has been released and electrode 40 has been retracted, dissection can continue using jaw parts 14 and 16.

As is evident from the description given above, instrument 10 can be disassembled into the following subassemblies: jaw parts 14, 16 with the associated actuation element 28, further electrode 40 with the associated actuation element 51, shaft 12, and handle 18.

Figure 8:
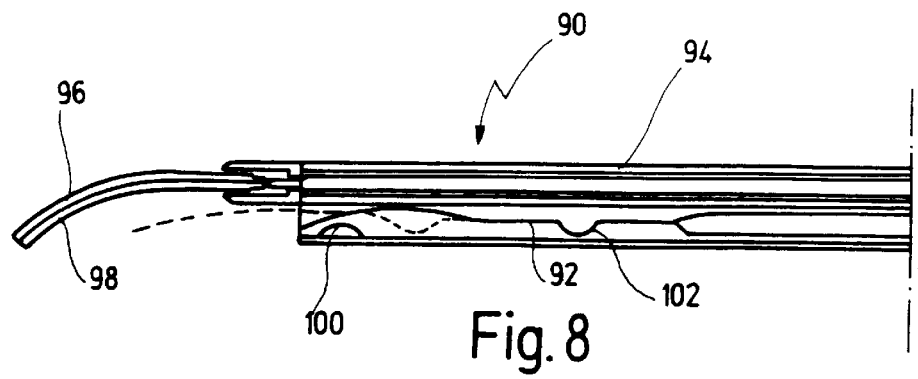
FIG. 8 shows the distal end of a further exemplary embodiment of an instrument, in a sectioned representation corresponding to FIG. 2.
Figure 9:
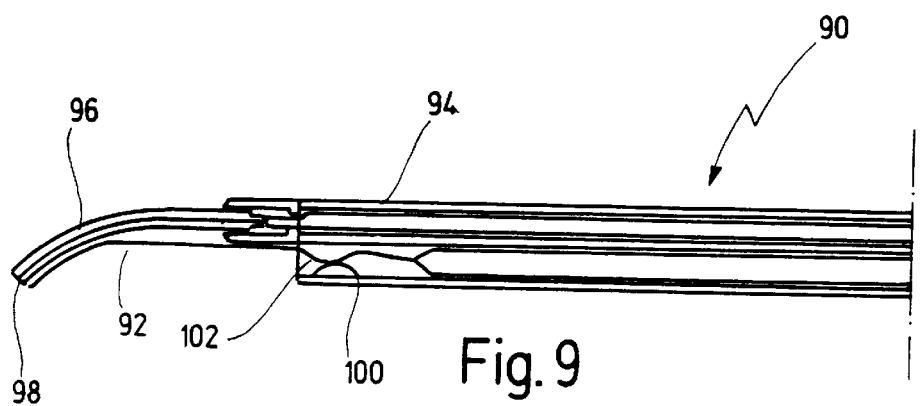
FIG. 9 shows the distal end in FIG. 8 in a representation corresponding to FIG. 3, in which the further electrode is advanced into its distal position.

FIGS. 8 and 9 depict a further exemplary embodiment of an instrument 90 that differs from the previous exemplary embodiment only in terms of the configuration of a further electrode 92.

FIG. 8 shows further electrode 92 in its proximal position retracted into a shaft 94, while further electrode 92 in FIG. 9 is shown in its position displaced in the distal direction, in which it forms with jaw parts 96 and 98 a bipolar coagulation electrode arrangement.

Unlike further electrode 40, further electrode 92 is of at least partially flexible configuration. In the case of the exemplary embodiment shown in FIGS. 8 and 9, further electrode 92 is configured as a flat steel leaf spring, and is thus of entirely flexible configuration. A cam bevel 100 is configured at the distal end of shaft 94. Further electrode 92 also has a cam bevel 102 in the region of its proximal end.

As further electrode 92 is advanced, it initially describes a trajectory running substantially in the longitudinal direction of shaft 94, as shown in FIG. 8 with dashed lines. As further electrode 92 is advanced even further, cam bevel 102 then runs onto cam bevel 100, as a result of which further electrode 92 describes, in the last portion of its movement travel, a trajectory having a component directed toward jaw parts 96 and 98, so that further electrode 92 is actively pushed against jaw parts 96, 98. As a result, the tissue gripped between jaw parts 96, 98 and further electrode 92 is securely clamped for coagulation.

Figure 10:
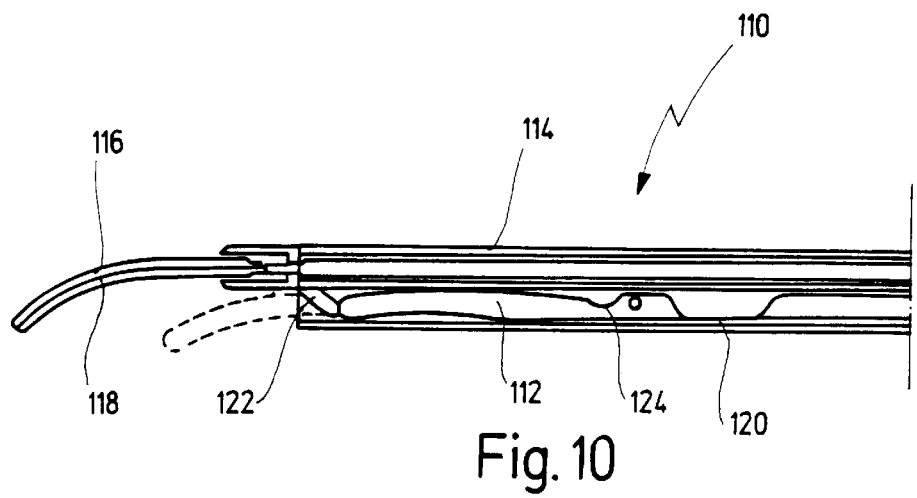
FIG. 10 shows the distal end of a further exemplary embodiment of an instrument, in a representation corresponding to FIG. 8.
Figure 11:
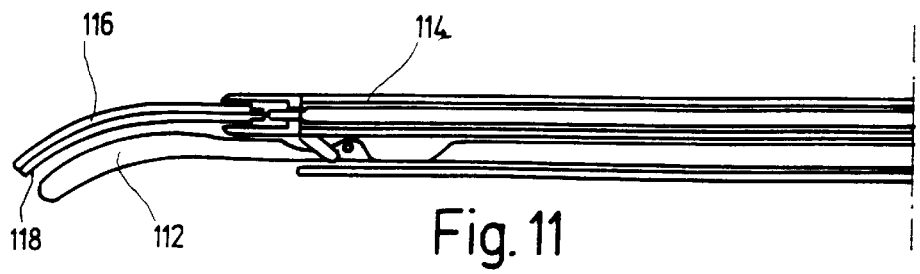
FIG. 11 shows the distal end in FIG. 10 in a representation corresponding to FIG. 9, in which the further electrode is advanced into its distal position.

Lastly, FIGS. 10 and 11 depict yet another exemplary embodiment of an instrument 110 that once again differs from the exemplary embodiments described earlier in terms of the configuration of a further electrode 112. Further electrode 112 is shown in FIG. 10 in its proximal position retracted in a shaft 114 of instrument 110, and in FIG. 11 in its position displaced in the distal direction. Instrument 110 once again has jaw parts 116 and 118 with which electrode 112, in the distal position shown in FIG. 11, forms a bipolar coagulation arrangement. Provision can once again be made for further electrode 112 to form a coagulation electrode arrangement of this kind with only one of jaw parts 116, 118.

In contrast to the previous exemplary embodiment, further electrode 112 is of partially flexible configuration, specifically in a proximal portion 120. Further electrode 112 is otherwise of rigid and solid configuration, and has approximately the shape of a knife but without sharp cutting edges.

Once again, a cam bevel 122 that is of slotted configuration in the longitudinal direction of shaft 114 is configured on shaft 114, further electrode 112 being guided longitudinally in the slot (not shown) as it is advanced.

As further electrode 112 is advanced, it runs over cam bevel 122 and thereby is initially spread away from jaw parts 116, 118, as shown in FIG. 10 with dashed lines; the result is to create a larger catching space between jaw parts 116, 118 and further electrode 112.

Further electrode 112 has an indentation 124 in the proximal region. As soon as indentation 124 reaches cam bevel 122 as further electrode 112 is advanced, further electrode 112 is deflected elastically toward jaw parts 116, 118. Further electrode 112 thus describes, as it is advanced, a trajectory that initially has a component directed away from jaw parts 116, 118 and, in the last portion of the movement travel, has a component directed toward jaw parts 116, 118.

What I claim, is:

1. A medical instrument for dissecting tissue in the human or animal body, comprising:

an elongated shaft having a distal end;

two jaw parts at said distal end of said shaft, said two jaw parts being movable relative to one another and configured to coact for dissecting said tissue, at least one of said two jaw parts being configured as an electrode which can be impinged upon by high-frequency current, wherein a further electrode which can be impinged upon by a high-frequency current is provided which can be optionally displaced from a retracted proximal position into a distal position adjacent to said two jaw parts in which position said further electrode forms in coaction with said at least one jaw part configured as an electrode one pole of an electrode arrangement for bipolar coagulation of said tissue.

2. The instrument of claim 1, wherein said two jaw parts are curved out of a longitudinal axis of said shaft, and said further electrode is arranged on a concave side of said jaw parts.

3. The instrument of claim 1, wherein said further electrode is of planar configuration and has approximately the same width dimension as said two jaw parts.

4. The instrument of claim 1, wherein said further electrode forms, with at least one of said jaw parts, a catching space for gripping tissue.

5. The instrument of claim 1, wherein said further electrode, in its retracted position, is received in recessed fashion in said shaft.

6. The instrument of claim 1, wherein said further electrode is beveled at its distal end on a side facing toward said jaw parts.

7. The instrument of claim 1, wherein said further electrode is of at least partially flexible configuration and describes, when advanced, a trajectory that initially runs approximately in longitudinal direction of said shaft with or without a component turned slightly away from said jaw parts, and before reaching said distal position runs with a component directed toward said jaw parts.

8. The instrument of claim 7, wherein there is arranged on said shaft a cam bevel onto which a cam bevel configured on said further electrode runs as said further electrode is advanced, thus pressing said further electrode toward said jaw parts in said distal position.

9. The instrument of claim 1, wherein said further electrode is of at least partially flexible configuration and describes, when advanced, a trajectory that initially runs approximately in longitudinal direction of said shaft with or without a component turned slightly away from said jaw parts, and before reaching said distal position runs with a component directed toward said jaw parts, and wherein a cam bevel is arranged on said shaft so that as said further electrode is advanced, it is first spread away from said jaw parts and, in said distal position, deflects elastically toward said jaw parts.

10. The instrument of claim 1, wherein there is arranged at a proximal end of said instrument a handle that has two grip elements for actuation of said jaw parts and a further grip element for actuation of said further electrode, said grip elements forming a grip arrangement operable with one hand.

11. The instrument of claim 10, wherein said further grip element is joined via a lever arrangement to said further electrode in such a way that by pulling said further grip element, said further electrode is displaced from its proximal into its distal position.

12. The instrument of claim 11, wherein said further electrode is preloaded into its proximal position, into which it automatically returns after said further grip element is released.

13. The instrument of claim 1, wherein there is arranged at a proximal end of said instrument a handle that has two grip elements for actuation of said jaw parts and a further grip element for actuation of said further electrode, said grip elements forming a grip arrangement operable with one hand, and wherein said further electrode is joined to said further grip element via an actuation element received in axially movable fashion in said shaft, said actuation element furthermore being joined via a wiper contact to a high-frequency current lead-in.

14. The instrument of claim 13, wherein said wiper contact allows the passage of current to said further electrode only when said further electrode has been advanced into or almost into said distal position.

15. The instrument of claim 1, wherein there is arranged at a proximal end of said instrument a handle that has two grip elements for actuation of said jaw parts and a further grip element for actuation of said further electrode, said grip elements forming a grip arrangement operable with one hand, and wherein said further electrode is joined to said further grip element via an actuation element received in axially movable fashion in said shaft, said actuation element furthermore being joined via a wiper contact to a high-frequency current lead-in, and wherein said actuation element is joined to said further grip element removably, preferably by snap-locking.

16. The instrument of claim 1, wherein there is arranged at a proximal end of said instrument a handle that has two grip elements for actuation of said jaw parts and a further grip element for actuation of said further electrode, said grip elements forming a grip arrangement operable with one hand, and wherein said jaw parts are removably joined to said grip elements by way of an actuation element received in axially movable fashion in said shaft.

17. The instrument of claim 1, wherein said jaw parts are joined to said distal end of said shaft via a bayonet closure.

18. The instrument of claim 1, wherein there is arranged at a proximal end of said instrument a handle that has two grip elements for actuation of said jaw parts and a further grip element for actuation of said further electrode, said grip elements forming a grip arrangement operable with one hand, and wherein it can be disassembled into subassemblies made up of said jaw parts with said actuation element joined thereto, said further electrode with said further actuation element, said handle, and said shaft.

* * * * *